(12) United States Patent
Neumann et al.

(10) Patent No.: US 11,980,478 B2
(45) Date of Patent: May 14, 2024

(54) SELF-ADHESIVE ELECTRODE PATCH

(71) Applicant: Heraeus Deutschland Gmbh & Co. KG, Hanau (DE)

(72) Inventors: Christian Neumann, Hungen (DE); Armin Sautter, Düsseldorf (DE); Tim Asmus, Allendorf/Lumda (DE)

(73) Assignee: HERAEUS DEUTSCHLAND GMBH & CO. KG, Hanau (DE)

( * ) Notice: Subject to any disclaimer, the term of this patent is extended or adjusted under 35 U.S.C. 154(b) by 1051 days.

(21) Appl. No.: 16/633,970

(22) PCT Filed: Jul. 23, 2018

(86) PCT No.: PCT/EP2018/069933
§ 371 (c)(1),
(2) Date: Jan. 24, 2020

(87) PCT Pub. No.: WO2019/020571
PCT Pub. Date: Jan. 31, 2019

(65) Prior Publication Data
US 2020/0214632 A1     Jul. 9, 2020

(30) Foreign Application Priority Data
Jul. 27, 2017 (EP) .................................. 17183580

(51) Int. Cl.
*A61B 5/00* (2006.01)
*A61L 24/06* (2006.01)
(Continued)

(52) U.S. Cl.
CPC ............ *A61B 5/6833* (2013.01); *A61L 24/06* (2013.01); *C09J 9/02* (2013.01); *C09J 11/08* (2013.01);
(Continued)

(58) Field of Classification Search
CPC .................................................. A61B 5/6833
See application file for complete search history.

(56) References Cited

U.S. PATENT DOCUMENTS 7,136,691 B2   11/2006 Menon
7,742,828 B2    6/2010 Gadsby et al.
(Continued)

FOREIGN PATENT DOCUMENTS

| CN | 1518569 | 8/2004 |
| CN | 105939659 | 9/2016 |

(Continued)

OTHER PUBLICATIONS

Chinese Office Action dated Jun. 4, 2021 for Chinese Patent Application 201880049518.0.
(Continued)

*Primary Examiner* — William D Young
(74) *Attorney, Agent, or Firm* — Panitch Schwarze Belisario & Nadel LLP (57) ABSTRACT

Disclosed is a layered body comprising a polymer comprising repeating units having the general structure $-CH_2-CHR^1-COOR^2-$ as defined herein, to a process for producing such a layered body, to a layered body produced by that process and to the use of a layered body for electrophysical measurements.

12 Claims, 2 Drawing Sheets

(51) Int. Cl.

| | | |
|---|---|---|
| *C09J 9/02* | (2006.01) | |
| *C09J 11/08* | (2006.01) | |
| *C09J 133/08* | (2006.01) | |
| *A61B 5/0536* | (2021.01) | |
| *A61B 5/259* | (2021.01) | |
| *A61B 5/291* | (2021.01) | |
| *A61B 5/296* | (2021.01) | |
| *A61B 5/398* | (2021.01) | |

(52) U.S. Cl.
CPC ........... *C09J 133/08* (2013.01); *A61B 5/0536* (2013.01); *A61B 5/259* (2021.01); *A61B 5/291* (2021.01); *A61B 5/296* (2021.01); *A61B 5/398* (2021.01); *A61B 2562/0209* (2013.01); *A61B 2562/0215* (2017.08); *Y10T 428/2891* (2015.01)

(56) References Cited

U.S. PATENT DOCUMENTS

| | | | | |
|---|---|---|---|---|
| 8,013,092 B1* | 9/2011 | Krajnik | ................ | C09D 133/14 |
| | | | | 526/317.1 |
| 9,050,451 B2 | 6/2015 | Hubertus et al. | | |
| 9,159,940 B2 | 10/2015 | Kato et al. | | |
| 9,299,476 B2 | 3/2016 | Green et al. | | |
| 10,153,065 B2 | 12/2018 | Tsukada et al. | | |
| 2006/0202171 A1* | 9/2006 | Yoshida | ...................... | C08J 3/09 |
| | | | | 252/500 |
| 2009/0005667 A1 | 1/2009 | Cui et al. | | |
| 2015/0348671 A1 | 12/2015 | Fujiki et al. | | |
| 2016/0196892 A1* | 7/2016 | Ohori | ...................... | G06F 3/041 |
| | | | | 345/173 |
| 2016/0338645 A1* | 11/2016 | Tsukada | ................. | A61B 5/282 |

FOREIGN PATENT DOCUMENTS

| | | |
|---|---|---|
| CN | 108841097 | 11/2018 |
| DE | 102008050932 | 4/2009 |
| EP | 2622018 | 8/2013 |
| EP | 3100678 | 12/2016 |
| EP | 3318589 | 5/2018 |
| EP | 3354689 | 8/2018 |
| JP | 2000060815 | 2/2000 |
| JP | 2001299713 | 10/2001 |
| JP | 2016106187 | 6/2016 |
| KR | 101419018 | 8/2014 |
| TW | 201546979 | 12/2015 |
| WO | 200009203 | 2/2000 |
| WO | 2003000765 | 1/2003 |
| WO | 2012043025 | 4/2012 |
| WO | 2015115440 | 6/2015 |
| WO | 2016144751 | 9/2016 |

OTHER PUBLICATIONS

Scher et al., "Critical Density in Percolation Processes", J Chem Phys, 1970, 53, pp. 3759-3761.
Taiwanese Office Action dated Dec. 23, 2021 for Taiwanese Patent Application 107125850.
Kim et al., "Waterborne Polyacrylic/PEDOT Nanocomposites for Conductive Transparent Adhesives", Journal of Nanoscience and Nanotechnology, 2013, 13, pp. 7631-7636.
Korean Office Action dated Jan. 7, 2021 for Korean Patent Application 10-2020-7003508.
Japanese Office Action dated Mar. 9, 2021 for Japanese Patent Application 2020-501827.
Leleux et al., "Ionic Liquid Gel-Assisted Electrodes for Long-Term Cutaneous Recordings", Adv Healthcare Mater, 2014, 3, pp. 1377-1380.
International Search Report and Written Opinion dated Oct. 26, 2018 for International Patent Application PCT/EP2018/069933.
Muller, "Automated determination of particle-size distributions of dispersions by analytical ultracentrifugation", Colloid & Polymer Science, 1989, 267, pp. 1113-1116.
Scholtan et al., "Determination of the particle size distribution of latices with an ultracentrifuge", Kollid-Z u Z Polymere, 1972, 250, pp. 782-796.
Acronal S 728 Safety Data Sheet, BASF, 2019, pp. 1-9.
BTC Chemical Distribution, "Dispersions for Adhesives and Construction", Europe, pp. 1-16.
BTC Chemical Distribution, Aqueous dispersions (Latex) for technical applications, 2022. pp 1-3.

* cited by examiner

2a  2b

SELF-ADHESIVE ELECTRODE PATCH

CROSS REFERENCE TO RELATED APPLICATIONS

This application is a U.S. national phase filing of International Patent Application Number PCT/EP2018/069933 filed Jul. 23, 2018 that claims the priority of European Patent Application Number 17183580.4 filed Jul. 27, 2017. The disclosures of these applications are hereby incorporated by reference in their entirety.

TECHNICAL FIELD

The present invention relates to a layered body that, for example, can be used as an self-adhesive electrode patch, to a dispersion by means of which such a layered body can be prepared, to a process for the production of such a layered body, to a layered body obtainable by that process, to the use of a layered body for electrophysical measurements and to a therapeutic current delivery or current receiving system.

BACKGROUND

Skin surface electrodes are important components in many medical diagnostic systems including, for example, electrocardiography (ECG), electromyography (EMG), and electroencephalography (EEG). In these systems, the electrode plays a critical role as a transducer converting physiological variables, such as those of the heart, muscles and brain, respectively, in ECG, EMG and EEG, to electrical potentials. The measured potentials are then amplified and processed by an instrument, such as an electronic measuring circuit and a computer.

State of the art in the field of current-carrying and/or dissipating body electrodes optimized for short-term applications are systems that are based on aqueous gel electrolytes, such as those disclosed in U.S. Pat. No. 9,050,451 B1. However, such gel-based electrodes are disadvantageous with respect to the attachment of the electrodes to the skin as well as with respect to the long-term stability. When attaching these electrodes to the skin of a patient care has to be taken that the liquid electrolyte does not come into contact with the adhesive parts in order to avoid that the adhesive properties of the electrode and thus the contact between the electrode and the skin are not negatively affected. Furthermore, gel electrolytes are usually acidic aqueous systems comprising, for example, ascorbic acid or its derivatives. The presence of such acidic compounds, however, leads to side effects such as erythema or skin irritation if the electrodes are used for long-term applications.

As an alternative for long-term applications electrodes are known in the prior art that are based on polymers comprising carbon, such as the graphite loaded polymers disclosed in U.S. Pat. No. 7,136,691 B2, or electrodes that are based on conductive liquid elastomers filled with metallic particles, such as the rubber compositions disclosed in DE 10 2008 050 932 A1. However, electrodes based on these conductive polymer systems require a certain lead time of approximately 30 min after application to the skin in order to achieve reliable results. This is due to the change in the transition resistances due to both geometrical and moisture-induced changes in the interface to the skin.

It is also known in the prior art that doped thiophenes such as PEDOT/PSS can be used as conductive materials in body electrodes. Leleux et al. (*Adv. Healthcare Mater,* 2014, 3, pages 1377-1380) disclose ionic liquid gel-assisted electrodes for long-term cutaneous recordings, in which an ionic liquid gel was incorporated onto electrodes made of Au and PEDOT/PSS. These electrodes were deposited on a thin film of parylene C to render them conformable to the skin.

However, these polymer-based electrode systems are characterized in that their conductivity is comparatively low. For this reason complex metallic conductive structures such as those disclosed in U.S. Pat. No. 7,742,828 are preferably used in the state of the art for the most homogenous potential distribution possible. However, the fabrication of these metallic conductive structures is complex and thus cost-intensive.

OBJECTS OF THE INVENTION

The present invention was based on the object of overcoming the disadvantages resulting from the prior art in connection with skin surface electrodes.

In particular, the present invention was based on the object of providing a layered body that can be used for the skin contact in a skin surface electrode that can easily be applied to the skin and that even in case of a long-term application does not negatively affect the skin. The transition resistances of these skin surface electrodes should preferably not be changed due to moisture-absorption of the electrodes, making them particularly suitable for long-term measurements.

The present invention was also based on the object of providing a layered body that can be used for the skin contact in a skin surface electrode by means of which reliable results can be obtained immediately after application of the electrode to the skin. Furthermore, the layered body should be characterized in that it can be used in long-term applications and in that its electrical properties, particularly its lateral and transversal resistance, are not significantly affected by parameters such as the body temperature or the humidity of the environment. In this context it would be particularly advantageous if the layered body can be used for the skin contact in a skin surface electrode without the necessity of adding liquid electrolytes.

The present invention was also based on the object of providing a dispersion that can be used for the preparation of such a layered body. A further object underlying the present intention is to provide a process by means of which such a layered body can be prepared in an efficient and cost-efficient manner, preferably in an automatable mass production process.

SUMMARY

A contribution to achieving at least one of the above described objects is made by the subject matter of the category forming claims of the present invention. A further contribution is made by the subject matter of the dependent claims which represent specific embodiments of the invention.

A contribution towards achieving the abovementioned objects is also made by a layered body comprising
(I) a substrate;
(II) a conductive adhesive layer, preferably a conductive adhesive layer that is self-adhesive to the human skin, and that is superimposed on at least a part of at least one surface of the substrate, wherein the conductive adhesive layer comprises IIa) a polymer comprising repeating units having the general structure wherein
R$^1$ represent H or an alkyl group, preferably H or CH$_3$, most preferably H, and
R$^2$ represents an optionally substituted C$_1$-C$_{10}$-alkyl group, preferably a group selected from the group consisting of —CH$_3$, —CH$_2$CH$_3$, —C$_4$H$_9$, —CH$_2$CH(C$_2$H$_5$)(C$_4$H$_9$) and —C$_8$H$_{17}$,
and wherein the polymer forms a matrix of the conductive adhesive layer;
IIb) particles of a conductive polymer, preferably particles of a complex of a cationic polythiophene and a polymeric anion, that are distributed in the matrix;
wherein the conductive adhesive layer is characterized by
a specific resistance in transversal direction (R$_{transversal}$) of less than 500 Ωm, preferably less than 100 Ωm and most preferably less than 50 Ωm, and
a specific resistance in lateral direction (R$_{lateral}$) of less than 5000 Ωm, preferably less than 50 Ωm and most preferably less than 5 Ωm.

|2| The dispersion according to |1|, wherein the polymer of particles A) has a glass transition temperature of less than 35° C., preferably less than 20° C., more preferably less than 10° C. and most preferably less than 0°.

|3| The dispersion according to embodiment |1| or |2|, wherein the particles A) have a mass average particle diameter in the range from 1000 to 5000 nm, preferably in the range from 1000 to 4000 nm and most preferably in the range from 1000 to 3000 run.

|4| The dispersion according to anyone of embodiments |1| to |3|, wherein R$^1$ is H and R$^2$ is selected from the group consisting of —CH$_3$, —CH$_2$CH$_3$, —C$_4$H$_9$, —CH$_2$CH(C$_2$H$_5$)(C$_4$H$_9$) and —C$_8$H$_{17}$.

|6| The dispersion according to anyone of embodiments |1| to |4|, wherein at least 25%, preferably at least 35%, more preferably at least 45% and most preferably at least 55% of the repeating units in the polymer of particles A) are monomers in which R$^1$ is H and R$^2$ is selected from the group consisting of —CH$_3$, —CH$_2$CH$_3$, —C$_4$H$_9$, —CH$_2$CH(C$_2$H$_5$)(C$_4$H$_9$) and —C$_8$H$_{17}$, based on the total number of repeating units in the polymer of particles A).

|6| The dispersion according to anyone of embodiments |1| to |5|, wherein the polymer of particles A) is a copolymer of acrylic acid or a salt of acrylic acid or both and an acrylic acid ester.

|7| The dispersion according to anyone of embodiments |1| to |6|, wherein the polymer of particles A) is a copolymer of acrylic acid or a salt of acrylic acid or both and an acrylic acid ester selected from the group consisting of methyl acrylate, ethyl acrylate, n-butyl acrylate, 2-ethylhexylacrylate and n-octyl acrylate.

|8| The dispersion according to anyone of embodiments |1| to |7|, wherein the dispersion comprises the polymer of particles A) in an amount in the range from 10 to 80 wt. %, preferably in the range from 15 to 75 wt. %, more preferably in the range from 20 to 70 wt. % and most preferably in the range from 25 to 65 wt. %, in each case based on the total weight of the dispersion.

|9| The dispersion according to anyone of embodiments |1| to |8|, wherein the particles B) have a mass average particle diameter in the range from 25 to 125 nm, preferably in the range from 50 to 125 nm and most preferably in the range from 75 to 125 nm.

|10| The dispersion according to anyone of embodiments |1| to |9|, wherein the conductive polymer of particles B) comprises a PEDOT/PSS-complex.

|11| The dispersion according to anyone of embodiments |1| to |10|, wherein the dispersion comprises the conductive polymer, preferably the cationic polythiophene and the polymeric anion, most preferably PEDOT/PSS, in a total amount in the range from 0.01 to 5 wt. %, preferably in the range from 0.025 to 3.5 wt. %, more preferably in the range from 0.05 to 2 wt. % and most preferably in the range from 0.1 to 1 wt. %, in each case based on the total weight of the dispersion.

|12| The dispersion according to anyone of embodiments |1| to |11|, wherein the dispersion further comprises, as component iv), a polar high boiling compound having a boiling point (at 1013 mbar) of at least 120° C., preferably at least 140° C. and most preferably at least 160° C.

|13| The dispersion according to embodiment |12|, wherein the polar high boiling compound is selected from the group consisting of a diol, preferably an alkylene glycol, a triol, preferably glycerol, and a sulfoxide, preferably DMSO.

|14| The dispersion according to embodiment |13|, wherein the polar high boiling compound is ethylene glycol.

|15| The dispersion according to anyone of embodiments |12| to |14|, wherein the dispersion comprises the polar high boiling compound, preferably ethylene glycol, in an amount in the range from 0.1 to 20 wt. %, preferably in the range from 0.5 to 17.5 wt. %, more preferably in the range from 1 to 15 wt. % and most preferably in the range from 5 to 12.5 wt. %, in each case based on the total weight of the dispersion.

|16| The dispersion according to anyone of embodiments |12| to |15|, wherein the weight ratio of the polar high boiling compound to the total weight of the cationic polythiophene and the polymeric anion in particles B) (polar high boiling compound:(cationic polythiophene+polymeric anion)) is at least 1:1, preferably at least 3:1, more preferably at least 6:1 and most preferably at least 9:1.

|17| The dispersion according to anyone of embodiments |1| to |16|, wherein the dispersion is an aqueous dispersion comprising water as a dispersant.

|1| A dispersion comprising particles A) of polymer comprising repeating units having the general structure —CH$_2$—CR$^1$—COOR$^2$— wherein R$^1$ represent H or an alkyl group, preferably H or CH$_3$, most preferably H, and R$^2$ represents an optionally substituted C 1-C 10-alkyl group, preferably a group selected from the group consisting of —CH$_3$, —CH$_2$CH$_3$, —C$_4$H$_9$, —CH$_2$CH(C$_2$H$_5$)(C$_4$H$_9$) and —C$_8$H$_{17}$, wherein particles A) have a mass average particle diameter (d50) of at least 500 nm, preferably at least 600 nm, more preferably at least 700 nm, more preferably at least 800 nm, more preferably at least 900 nm and most preferably at least 1000 nm; particles B) of a conductive polymer, preferably particles B) of a complex of a cationic polythiophene and a polymeric anion, wherein the particles B) have a mass average particle diameter of less than 150 nm, preferably less than 145 nm, more preferably less than 140 nm, more preferably less than 135 nm, more preferably less than 130 nm and most preferably less than 125 nm; at least one dispersant, preferably water, wherein the weight ratio of the polymer in particles A) to the conductive polymer in particles B), preferably the weight ratio of the polymer in particles A) to the total weight of the cationic polythiophene and the polymeric anion in the complex of particles B) is at least 5:1, preferably at least 10:1, more preferably at least 15:1, more preferably at least 20:1 and most preferably at least 25:1.

|19| The layered body according to embodiment |18|, wherein the substrate comprises a non-conductive polymer layer and a further conductive layer that is in contact with at least a part of at least one surface of the non-conductive polymer layer, wherein the conductive adhesive layer is in contact with at least a part of the further conductive layer.

|20| The layer body according to embodiment |18| or |19|, wherein the non-conductive polymer layer is a polyimide layer having a thickness in the range from 1 to 50 μm, preferably in the range from 3 to 40 μm, more preferably in the range from 6 to 30 μm and most preferably in the range from 10 to 20 μm.

|21| The layer body according to anyone of embodiments |18| to |20|, wherein the further conductive layer is a silver grid.

|22| The layered body to anyone of embodiments |18| to |21|, wherein polymer IIa) has a glass transition temperature of less than 35° C., preferably less than 20° C., more preferably less than 10° C. and most preferably less than 0°.

|23| The layered body according to anyone of embodiments |16| to |20|, wherein $R^1$ is H and $R^2$ is selected from the group consisting of —$CH_3$, —$CH_2CH_3$, —$C_4H_9$, —$CH_2CH(C_2H_5)(C_4H_9)$ and —$C_8H_{17}$.

|24| The layered body according to anyone of embodiments |18| to |23|, wherein at least 25%, preferably at least 35%, more preferably at least 45% and most preferably at least 55% of the repeating units in polymer IIa) are monomers in which $R^1$ is H and $R^2$ is selected from the group consisting of —$CH_3$, —$CH_2CH_3$, —$C_4H_9$, —$CH_2CH(C_2H_5)(C_4H_9)$ and —$C_8H_{17}$, based on the total number of repeating units in polymer IIa).

|25| The layered body according to anyone of embodiments |18| to |24|, wherein polymer IIa) is a copolymer of acrylic acid or a salt of acrylic acid or both and an acrylic acid ester.

|26| The layered body according to anyone of embodiments |18| to |25|, wherein polymer IIa) is a copolymer of acrylic acid or a salt of acrylic acid or both and an acrylic acid ester selected from the group consisting of methyl acrylate, ethyl acrylate, n-butyl acrylate, 2-ethylhexylacrylate and n-octyl acrylate.

|27| The layered body according to anyone of embodiments |18| to |26|, wherein the matrix comprises a plurality of islands of the polymer IIa), the islands having a size of at least $1\times10^{-6}$ mm$^2$, preferably of at least $1\times10^{-5}$ mm$^2$, more preferably of at least $1\times10^{-4}$ mm$^2$ and most preferably of at least $1\times10^3$ mm$^2$.

|28| The layered body according to anyone of embodiments |18| to |27|, wherein particles IIb) are PEDOT/PSS-particles.

|29| The layered body according to anyone of embodiments |18| to |28|, wherein the weight ratio of polymer IIa) to the total weight of the cationic polythiophene and the polymeric anion in particles IIb) (polymer IIa):(cationic polythiophene+polymeric anion)) in the conductive adhesive layer is at least 5:1, preferably at least 10:1, more preferably at least 15:1, more preferably at least 20:1 and most preferably at least 25:1.

|30| The layered body according to anyone of embodiments |16| to |28|, wherein the conductive adhesive layer has a thickness in the range from 1 to 500 μm, preferably in the range from 3 to 250 μm, more preferably in the range from 4 to 150 μm and most preferably in the range from 5 to 50 μm.

|31| A process for producing a layered body, the process comprising α1) providing a dispersion as defined in anyone of embodiments |1| to |17|, preferably providing a dispersion as defined in anyone of embodiments |12| to |16|; α2) applying the dispersion onto at least a part of at least one surface of a substrate; α3) at least partial removal of the dispersant iii) for the formation of a conductive adhesive layer, preferably for the formation of a conductive adhesive layer that is self-adhesive to the human skin, and that is superimposed on at least a part of at least one surface of the substrate, wherein the at least partial removal of the dispersant is accomplished by heating the dispersion that has been applied onto the substrate to a temperature above the glass transition temperature of the polymer of particles A).

|32| The process according to embodiment |31|, wherein the polymer of particles A) has a glass transition temperature of less than 35° C., preferably less than 20° C., more preferably less than 10° C. and most preferably less than 0°.

|33| The process according to embodiment |31| or |32|, wherein the substrate is as defined in embodiments |19| to |21|.

|34| A layered body obtainable by the process according to anyone of embodiments |31| to |33|.

|35| The layered body according to embodiment |34|, wherein the conductive adhesive layer comprises a matrix of the polymer of particles A), in which the particles B) of the conductive polymer, preferably the particles of a complex of a cationic polythiophene and a polymeric anion, are distributed.

|36| The layered body according to embodiment |34| or |35|, wherein the conductive adhesive layer is characterized by a specific resistance in transversal direction ($R_{transversal}$) of less than 500 Ωm, preferably less than 100 Ωm and most preferably less than 50 Ωm, and a specific resistance in lateral direction ($R_{lateral}$) of less than 5000 Ωm, preferably less than 50 Ωm and most preferably less than 5 Ωm.

|37| The layered body according to anyone of embodiments |34| to |36|, wherein the conductive adhesive layer has a thickness in the range from 1 to 500 μm, preferably in the range from 3 to 150 μm, more preferably in the range from 4 to 150 μm and most preferably in the range from 5 to 50 μm.

|38| Use of the layered body according to anyone of embodiments |18| to |30| and |34| to |37| for electrophysical measurements, wherein the conductive adhesive layer comes into direct contact with the skin.

|39| The use according to embodiment |38|, wherein the electrophysical measurement comprises electrocardiography (ECG), electroencephalography (EEG), electrical impedance tomography (EIT), electromyography (EMG) and electro-oculography (EOG).

|40| A therapeutic current delivery or current receiving system comprising: a therapeutic current delivery or current receiving device; at least one cable connector connected to the therapeutic current delivery or current receiving device; at least one electrode comprising a layered body to anyone of embodiments |18| to |30| and |34| to |37| connected to the at least one cable connector.

DETAILED DESCRIPTION

|18| A layered body comprising a substrate; a conductive adhesive layer, preferably a conductive adhesive layer that is self-adhesive to the human skin, and that is superimposed on at least a part of at least one surface of the substrate, wherein the conductive adhesive layer comprises II) a polymer comprising repeating units having the general structure —$CH_2$—$CR^1$—$COOR^2$—, wherein $R^1$ represent H or an alkyl group, preferably H or $CH_3$, most preferably H, and $R^2$ represents an optionally substituted $C_1$-$C_{10}$-alkyl group, preferably a group selected from the group consisting of —$CH_3$, —$CH_2CH_3$, —$C_4H_9$, —$CH_2CH(C_2H_5)(C_4H_9)$ and —$C_8H_{17}$, and wherein the polymer forms a matrix of the conductive adhesive layer;

IIb) particles of a conductive polymer, preferably particles of a complex of a cationic polythiophene and a polymeric anion, that are distributed in the matrix;

wherein the conductive adhesive layer is characterized by
a specific resistance in transversal direction ($R_{transversal}$) of less than 500 Ωm, preferably less than 100 Ωm and most preferably less than 50 Ωm, and
a specific resistance in lateral direction ($R_{lateral}$) of less than 5000 Ωm, preferably less than 50 Ωm and most preferably less than 5 Ωm.

Surprisingly, it has been discovered that the very special combination of conductive polymer particles, particularly PEDOT/PSS-particles, having a finer particles size with a $d_{50}$-value of less than 150 nm, and polyacrylate-based particles with a do-value of at least 500 nm allow the formation of a conductive adhesive layer that is self-adhesive to the human skin and that is characterized by outstanding electrical properties, particularly by a purely ohmic behaviour. These conductive adhesive layers do not require that addition of liquid electrolytes and the relevant resistances are also lower than for the known electrolyte-based electrode systems. Also, these conductive adhesive layers show a only negligible absorption of water when being stored under a humid atmosphere, which in turn also makes them particularly suitable as contact materials for body electrodes as the transition resistance is not affected by moisture-induced changes in the interface to the skin.

Component i)

A contribution towards achieving the abovementioned objects is made by a dispersion comprising particles A) of polymer comprising repeating units having the general structure —$CH_2$—$CR^1$—$COOR^2$— wherein $R^1$ represent H or alkyl, preferably H or $CH_3$, most preferably H, and $R^2$ represents an optionally substituted $C_1$-$C_{10}$-alkyl group, preferably a group selected from the group consisting of —$CH_3$, —$CH_2CH_3$, —$C_4H_9$, —$CH_2CH(C_2H_5)(C_4H_9)$ and —$C_8H_{17}$, wherein particles A) have a mass average particle diameter ($d_{50}$) of at least 500 nm, preferably at least 600 nm, more preferably at least 700 nm, more preferably at least 800 nm, more preferably at least 900 nm and most preferably at least 1000 nm; particles B) of a conductive polymer, preferably particles B) of a complex of a cationic polythiophene and a polymeric anion, wherein the particles B) have a mass average particle diameter of less than 150 nm, preferably less than 145 nm, more preferably less than 140 nm, more preferably less than 135 nm, more preferably less than 130 nm and most preferably less than 125 nm; at least one dispersant, preferably water; wherein the weight ratio of the polymer in particles A) to the conductive polymer in particles B), preferably the weight ratio of the polymer in particles A) to the total weight of the cationic polythiophene and the polymeric anion in the complex of particles B) is at least 5:1, preferably at least 10:1, more preferably at least 15:1, more preferably at least 20:1 and most preferably at least 25:1.

The polymer of particles A) is a polymer of acrylic acid esters or methacrylic acid esters or a copolymer of (meth)acrylic acid esters and one of more ethylenically unsaturated monomers that can be copolymerized with (meth)acrylic acid esters. The term "(meth)acrylic acid" in this text stands for methacrylic acid and acrylic acid, preferably for acrylic acid. Suitable polymers of particles A) include polymers such as poly(methyl(meth)acrylate) (PMMA or PMA), poly (ethyl(meth)-acrylate), poly-(butyl(meth)acrylate), poly (isobutyl(meth)acrylate), poly(hexyl-(meth)acrylate), poly (isodecyl(meth)acrylate), poly(lauryl(meth)acrylate), poly-(phenyl(meth)acrylate), poly(methyl acrylate), poly (isopropyl acrylate), poly-(isobutyl acrylate), poly (octadecyl acrylate) (jointly referred to herein as "polyacrylic acids"), or copolymers and mixtures thereof.

Particularly preferred polymers of particles A) are polymers comprising repeating units of the general structure shown above in which $R^1$ is H and $R^2$ is selected from the group consisting of —$CH_3$, —$CH_2CH_3$, —$C_4H_9$, —$CH_2CH(C_2H_5)(C_4H_9)$ and —$C_8H_{17}$, i.e., polymers or copolymers based on methyl acrylate, ethyl acrylate, n-butyl acrylate, 2-ethylhexylacrylate, n-octyl acrylate or mixtures of these compounds as the monomer. In this context it is particularly preferred that at least 25%, preferably at least 35%, more preferably at least 45% and most preferably at least 55% of the repeating units in the polymer of particles A) are monomers in which $R^1$ is H and $R^2$ is selected from the group consisting of —$CH_3$, —$CH_2CH_3$, —$C_4H_9$, —$CH_2CH(C_2H_5)(C_4H_9)$ and —$C_8H_{17}$, based on the total number of repeating units in the polymer of particles A). In this context it is furthermore preferred that the polymer of particles A) is a copolymer of acrylic acid or a salt of acrylic acid or both and an acrylic acid ester, particularly preferred a copolymer of acrylic acid or a salt of acrylic acid or both and acrylic acid ester selected from the group consisting of methyl acrylate, ethyl acrylate, n-butyl acrylate, 2-ethylhexylacrylate, n-octyl acrylate.

According to a further embodiment of the dispersion according to the present invention the polymers of particles A) are either only slightly crosslinked or, according to a particularly preferred embodiment, not crosslinked at all. In this context it is also preferred that the polymer of particles A) has a Free Swell Capacity in Saline determined by gravimetry according to NWSP 240.0.R2 (15) of less than 10 g/g, more preferably less than 1 g/g and most preferably less than 0.1 g/g.

Particularly preferred polymers of particles A) are polymers having a glass transition temperature of less than 35° C., preferably less than 20° C., more preferably less than 10° C. and most preferably less than 0°.

Suitable polymers of particles A) are the polymer particles in commercially available polyacrylate dispersions such as RUCO-COAT® AC 1010 or RUCO-COAT® AC 2510 obtainable from the Rudolf GmbH, Geretsried, Germany, or polyacrylate dispersions such as AQUA POLYMER AQP 275 obtainable from Alberdingk Boley GmbH, Krefeld, Germany.

Preferably, the dispersion according to the present invention comprises the polymer of particles A) in an amount in the range from 10 to 80 wt. %, preferably in the range from 15 to 75 wt. %, more preferably in the range from 20 to 70 wt. % and most preferably in the range from 25 to 65 wt. %, in each case based on the total weight of the dispersion.

Component ii)

The dispersion according to the present invention comprises as component ii) particles B) of a conductive polymer, preferably particles B) of a complex of a cationic polythiophene and a polymeric anion, wherein the particles B) have a mass average particle diameter of less than 150 nm, preferably less than 145 nm, more preferably less than 140 nm, more preferably less than 135 nm, more preferably less than 130 nm and most preferably less than 125 nm.

According to a particularly preferred embodiment of the dispersion according to the present invention particles B) have a mass average particle diameter in the range from 25 to 125 nm, preferably in the range from 50 to 125 nm and most preferably in the range from 75 to 125 nm.

The conductive polymer can be a polymer selected from the group consisting of an optionally substituted polythiophene, an optionally polyaniline and an optionally substituted polypyrrole, wherein optionally substituted polythiophenes are particularly preferred as the conductive polymer.

Preferred polythiophenes are those having the general formula in which
A represents an optionally substituted $C_1$-$C_5$-alkylene radical,
R represents a linear or branched, optionally substituted $C_1$-$C_{18}$-alkyl radical, an optionally substituted $C_5$-$C_{12}$-cycloalkyl radical, an optionally substituted $C_6$-$C_{14}$-aryl radical, an optionally substituted $C_7$-$C_{18}$-aralkyl radical, an optionally substituted $C_1$-$C_4$-hydroxyalkyl radical or a hydroxyl radical, wherein 0 to 8 radicals R can be bonded to A and, in the case of more than one radical, can be identical or different.

The polythiophenes preferably in each case carry H on the end groups.

In the context of the invention, $C_1$-$C_5$-alkylene radicals A are preferably methylene, ethylene, n-propylene, n-butylene or n-pentylene. $C_1$-$C_{18}$-alkyl R preferably represent linear or branched $C_1$-$C_{18}$-alkyl radicals, such as methyl, ethyl, n- or iso-propyl, n-, iso-, sec- or tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, n-heptyl, n-octyl, 2-ethylhexyl, n-nonyl, n-decyl, n-undecyl, n-dodecyl, n-tridecyl, n-tetradecyl, n-hexadecyl or n-octadecyl, $C_5$-$C_{12}$-cycloalkyl radicals R represent, for example, cyclopentyl, cyclohexyl, cycloheptyl, cyclooctyl, cyclononyl or cyclodecyl, $C_5$-$C_{14}$-aryl radicals R represent, for example, phenyl or naphthyl, and $C_7$-$C_{18}$-aralkyl radicals R represent, for example, benzyl, o-, m-, p-tolyl, 2,3-, 2,4-, 2,5-, 2,6-, 3,4-, 3,5-xylyl or mesityl. The preceding list serves to illustrate the invention by way of example and is not to be considered conclusive.

In the context of the invention, numerous organic groups are possible as optionally further substituents of the radicals A and/or of the radicals R, for example alkyl, cycloalkyl, aryl, aralkyl, alkoxy, halogen, ether, thioether, disulphide, sulphoxide, sulphone, sulphonate, amino, aldehyde, keto, carboxylic acid ester, carboxylic acid, carbonate, carboxylate, cyano, alkylsilane and alkoxysilane groups and carboxamide groups.

Polythiophenes in which A represents an optionally substituted $C_2$-$C_3$-alkylene radical are particularly preferred. Poly(3,4-ethylenedioxythiophene) is very particularly preferred as the polythiophene.

The polythiophenes can be neutral or cationic, wherein cationic polythiophenes are particularly preferred. The term "cationic" only relates to the charges on the polythiophene main chain. The polythiophenes can carry positive and negative charges in the structural unit, depending on the substituent on the radicals R, the positive charges being on the polythiophene main chain and the negative charges optionally being on the radicals R substituted by sulphonate or carboxylate groups. In this context, the positive charges of the polythiophene main chain can be partly or completely satisfied by the anionic groups optionally present on the radicals R. Overall, in these cases the polythiophenes can be cationic, neutral or even anionic. Nevertheless, in the context of the invention they are all regarded as cationic polythiophenes, since the positive charges on the polythiophene main chain are the deciding factor. The positive charges are not shown in the formulae, since their precise number and position cannot be determined absolutely. However, the number of positive charges is at least 1 and at most n, where n is the total number of all recurring units (identical or different) within the polythiophene.

For compensation of the positive charge of the cationic polythiophene, it is preferred that particles B) further comprise a polymeric anion which is preferably based on polymers functionalized with acid groups. Anions of polymeric carboxylic acids, such as polyacrylic acids, polymethacrylic acid or polymaleic acids, or of polymeric sulphonic acids, such as polystyrenesulphonic acids and polyvinylsulphonic acids, are possible in particular as the polyanion. These polycarboxylic and sulphonic acids can also be copolymers of vinylcarboxylic and vinylsulphonic acids with other polymerizable monomers, such as acrylic acid esters and styrene. Polyanions which are furthermore possible are perfluorinated, colloid-forming polyanions, which are commercially obtainable, for example, under the name Nafion®. The molecular weight of the polymers which are functionalized with acid groups and supply the polyanions is preferably 1,000 to 2,000,000, particularly preferably 2,000 to 500,000. The polymers functionalized with acid groups or their alkali metal salts are commercially obtainable, e.g., polystyrenesulphonic acids and polyacrylic acids, or can be prepared by known processes (see e.g., Houben Weyl, Methoden der organischen Chemie, vol. E 20 Makromolekulare Stoffe, part 2, (1987), p. 1141 et seq.). A particularly preferred polyanion is an anion of polystyrene sulfonic acid.

The particles B) preferably comprise a complex of a cationic polythiophene and a polymeric anion, particularly preferably a PEDOT/PSS-complex. Such complexes are obtainable by polymerizing the thiophene monomers, preferably 3,4-ethylenedioxythiophene, oxidatively in an aqueous solution in the presence of the polymeric anions, preferably by oxidatively polymerizing 3,4-ethylenedioxythiophene in the presence of an anion of polystyrenesulphonic acid.

Preferably, the dispersion according to the present invention comprises the conductive polymer, preferably the cationic polythiophene and the polymeric anion, preferably PEDOT/PSS, in a total amount in the range from 0.01 to 5 wt. %, preferably in the range from 0.025 to 3.5 wt. %, more preferably in the range from 0.05 to 2 wt. % and most preferably in the range from 0.1 to 1 wt. %, in each case based on the total weight of the dispersion (in case of a complex of a cationic polythiophene and a polymeric anion the amounts given above refer to the sum of the weight of the cationic polythiophene and the polymeric anion).

Component iii)

The dispersion according to the present invention comprises as component iii) at least one dispersant.

Preferred dispersants are water, water-miscible solvents, in particular those selected from the group consisting aliphatic alcohols, such as methanol, ethanol, n-propanol and isopropanol, diacetone alcohols, aliphatic ketones, such as acetone and methyl ethyl ketone or a mixture of at least two of these solvents. The most preferred solvent, however, is water, which means that the dispersions according to the present invention are preferably aqueous dispersions. In this context it is particularly preferred, that at least 75 wt. %, more preferably at least 80 wt. %, even more preferably at least 85 wt. % and even more preferably at least 90 wt. % of the total amount of dispersants in the dispersion is water.

Component iv)

The dispersion according to the present invention may further comprise, as component iv), a polar high boiling compound having a boiling point (at 1013 mbar) of at least 120° C., preferably at least 140° C. and most preferably at least 160° C. Preferred compounds that can be used as component iv) are diols, preferably alkylene glycols, trios, preferably glycerol, and sulfoxides, preferably DMSO. Particularly preferred alkylene glycols are ethylene glycol, diethylene glycol, triethylene glycol, propylene glycol, dipropylene glycol or mixtures of at least two of these alkylene glycols, wherein ethylene glycol is most preferred. Preferably, the weight ratio of the polar high boiling compound to the total weight of the cationic polythiophene and the polymeric anion in particles B) (polar high boiling compound:(cationic polythiophene+polymeric anion)) is at least 1:1, preferably at least 3:1, more preferably at least 6:1 and most preferably at least 9:1.

The amount of the polar high boiling compound, preferably ethylene glycol, in the dispersion according to the present invention is preferably in the range from 0.1 to 20 wt. %, more preferably in the range from 0.5 to 17.5 wt. %, more preferably in the range from 1 to 15 wt. % and most preferably in the range from 5 to 12.5 wt. %, in each case based on the total weight of the dispersion.

Component v)

The dispersion according to the present invention may further comprise, as component v), at least one further additive being different from components i) to iv). Suitable additives v) are surface-active substances, e.g. anionic surfactants, such as e.g. alkylbenzenesulphonic acids and salts, paraffin sulphonates, alcohol sulphonates, ether sulphonates, sulphosuccinates, phosphate esters, alkyl ether carboxylic acids or carboxylates, cationic surfactants, such as e.g. quaternary alkylammonium salts, nonionic surfactants, such as e.g. linear alcohol ethoxylates, oxo alcohol ethoxylates, alkylphenol ethoxylates or alkyl polyglucosides, in particular surfactants that are commercially available under the trademarks Dynol® and Zonyl®, adhesion promoters, such as e.g. organofunctional silanes or hydrolysates thereof, e.g. 3-glycidoxypropyltrialkoxysilane, 3-amino-propyltriethoxysi-lane, 3-mercaptopropyltrimethoxysilane, 3-methacryloxypropylt-rimethoxy-silane, vinyltrimethoxysilane or octyltriethoxysilane, crosslinking agents, such as melamine compounds, masked isocyanates, functional silanes, e.g. tetraethoxysilane, alkoxysilane hydrolysates, e.g. based on tetraethoxysilane, epoxysilanes, such as 3-glycidoxypropyltrialkoxysilane, conductivity enhancers, e. g. compounds containing ether groups, such as e.g. tetrahydrofiuran, compounds containing lactone groups, such as γ-butyrolactone, 7-valerolactone, compounds containing amide or lactam groups, such as caprolactam, N-methylcaprolactam, N,N-dimethyl-acetamide, N-methylacetamide, N,N-dimethylformamide (DMF), N-methyl-formamide, N-methylformanilide, N-methylpyrrolidone (NMP), N-octyl-pyrrolidone, pyrrolidone, sulphones and sulphoxides, such as e.g. sulpholane (tetramethylene sulphone), dimethylsulphoxide (DMSO), sugars or sugar derivatives, such as e.g. sucrose, glucose, fructose, lactose, sugar alcohols, such as e.g. sorbitol, mannitol, furan derivatives, such as e.g. 2-furancarboxylic acid, 3-furancarboxylic acid, glycerol, diglycerol, triglycerol or tetraglycerol.

The amount of such further additives in the dispersion according to the present invention is preferably in the range from 0.1 to 15 wt. %, more preferably in the range from 0.5 to 12.5 wt. %, more preferably in the range from 0.75 to 10 wt. % and most preferably in the range from 1 to 5 wt. %, in each case based on the total weight of the dispersion.

The dispersion according to the present invention can be prepared by simply mixing a dispersion, preferably an aqueous dispersion, comprising the above described particles A), for example a dispersion such as RUCO-COAT® AC 1010 AQUA POLYMER AQP 275, with a dispersion, preferably an aqueous dispersion, comprising the above described particles B), for examples a PEDOT/PSS-dispersion such as Heraeus Clevios™ P HC V6 Screen, Heraeus Clevios™ P, Heraeus CleviosT P HC V4, Heraeus Clevios™ P Jet, Heraeus Clevios™ P Jet 700, Heraeus Clevios™ P Jet HC, Heraeus Clevios™ P Jet HC V2, Heraeus CleviosT P Jet N, Heraeus Clevios™ P Jet N V2, Heraeus CleviosT P Jet UA, Heraeus Clevios™ P T2, Heraeus Clevios=™ P VP AI 4083, Heraeus CleviosT P VP CH 8000, Heraeus CleviosT PH 1000, Heraeus CleviosT PH 500, Heraeus Clevios™ PH 510, Heraeus Clevios™ PH, Heraeus Clevios™ S HAT, Heraeus Clevios™ S V3, Heraeus Clevios™ S V3 HV or Heraeus Clevios™ S V4. Such PEDOT/PSS-dispersions are commercially available from the Heraeus Deutschland GmbH, Hanau, Germany. Optionally, the alkylene glycol (component iv)) and further additives (component v)) can be added to one or both of these dispersions before they are mixed or can be added separately to the mixture of these dispersions.

The dispersion according to the present invention comprises as component i) particles A) of polymer comprising repeating units having the general structure

—CH$_2$—CR$^1$—COOR$^2$— wherein

R$^1$ represent H or an alkyl group, preferably H or CH$_3$, most preferably H, and R$^2$ represents an optionally substituted C$_1$-C$_{10}$-alkyl group, preferably a group selected from the group consisting of —CH$_3$, —CH$_2$CH$_3$, —C$_4$H$_9$, —CH$_2$CH(C$_2$H$_5$)(C$_4$H$_9$) and —C$_8$H$_{17}$, wherein particles A) have a mass average particle diameter (d$_{50}$) of at least 500 nm, preferably at least 600 nm, more preferably at least 700 nm, more preferably at least 800 nm, more preferably at least 900 nm and most preferably at least 1000 nm. According to a particularly preferred embodiment of the dispersion according to the present invention particles A) have a mass average particle diameter in the range from 1000 to 5000 nm, preferably in the range from 1000 to 4000 nm and most preferably in the range from 1000 to 3000 nm.

Such a layered body is, for example, obtainable by applying the dispersion according to the present invention onto a substrate and by subsequently removing at least a part of the dispersant for the formation of a conductive adhesive layer.

Component I)

The layered body according to the present invention comprises, as component I), a substrate.

The substrate is preferably a flexible substrate that is characterized by a sufficient adaptability towards the human skin. Preferred materials for the substrate are plastic films, which conventionally have a thickness in the range from 2 to 200 µm, preferably in the range from 3 to 150 µm, more preferably in the range from 4 to 100 µm and most preferably in the range from 5 to 100 µm. Such plastic films can be based, for example, on polymers such as polycarbonates, polyesters such as for example PET and PEN (polyethylene terephthalate and polyethylene naphthalene dicarboxylate), copolycarbonates, polysulphones, polyether sulphones (PES), polyimides, polyamides, polyethylene, polypropylene or cyclic polyolefins or cyclic olefin copolymers (COC), polyvinyl chloride, polystyrene, hydrogenated styrene polymers or hydrogenated styrene copolymers. Particularly suitable materials for the substrate are materials such as myclar, flex PC, Kapton or polymer thick films (PTF). According to a particularly preferred embodiment of the layered body according to the present invention a polyimide film such as a commercially available Kapton-foil is used as the flexible substrate. Alternatively, a thin polymer layer may be deposited on an inorganic carrier substrate (such as glass) from appropriate polymer precursors. A polyimide film can, for example, be formed on a glass carrier substrate by thermic polycondensation of polyamidocarboxylic acid. This leads to particularly thin substrate layers in the region of approximately 10 µm, which are characterized by a negligible mechanical stiffness and by a good adaptability towards the skin surface.

According to a preferred embodiment of the layered body according to the present invention the substrate comprises a non-conductive polymer layer and a further conductive layer that is in contact with at least a part of at least one surface of the non-conductive polymer layer, wherein the conductive adhesive layer is in contact with at least a part of the further conductive layer. The further conductive layer serves to improve the lateral conductivity of the layered body. Preferably, the further conductive layer is a layer based on carbon, metals or metal particles, wherein these conductive materials are preferably present in the form of a grid. Possible metals in this context are all metals which are conventionally employed in electronic components for the production of linear, metallic structures (so-called "busbars"), such as, for example, aluminium, silver, gold or copper. In the case of a further conductive layer comprising metallic particles it is preferable for these to be applied in the form of pastes which comprise such metallic particles having a particle diameter of less than 10 µm. Conductive silver particles or copper particles are very particularly preferred in this connection. If pastes which, in addition to the metallic particles, in particular can comprise solvents and binders are used, it is furthermore preferable for these pastes to be applied via screen printing processes. Also suitable for the formation of the further conductive layer are metallic layers such as a copper layer, a gold layer or am aluminum layer that can be applied onto the non-conductive polymer layer by vacuum deposition. Furthermore, the further conductive layer can also be formed by means of inks that are based on metallo-organic materials, for examples inks comprising metal carboxylates and/or inks comprising metallic nanoparticles or nanowires. Such inks can, for example, be applied onto the substrate by digital inkjet printing.

According to a particularly preferred embodiment of the layered body according to the present invention the non-conductive polymer layer is a polyimide layer having a thickness in the range from 1 to 50 µm, preferably in the range from 3 to 40 µm, more preferably in the range from 6 to 30 µm and most preferably in the range from 10 to 20 µm. The further conductive layer preferably is a silver grid, more preferably a silver grid that has been applied onto such a polyimide layer by means of a silver paste.

Component II)

The layered body according to the present invention comprises, as component II), a conductive adhesive layer, preferably a conductive adhesive layer that is self-adhesive to the human skin, and that is superimposed on at least a part of at least one surface of the substrate. This conductive adhesive layer comprises a polymer IIa) that, with respect to its chemical composition and also with respect to its glass transition temperature, preferably corresponds to the polymer of particles A) that has been described in detail above in connection with the dispersion according to the present invention. In the conductive adhesive layer of the layered body according to the present invention polymer IIa) forms the matrix of the conductive adhesive layer in which the particles IIb) of a conductive polymer, preferably the particles IIb) of a complex of a cationic polythiophene and a polymeric anion, are distributed. Preferred conductive polymers and preferred complexes of a cationic polythiophene and a polymeric anion are again those conductive polymers and those complexes that have already been described above in connection with the dispersion according to the present invention as preferred conductive polymers and complexes of particles B).

According to a particularly preferred embodiment of the layered body according to the present invention the matrix of the conductive adhesive layer comprises a plurality of islands of the polymer IIa), the islands having a size of at least $1 \times 10^{-6}$ µm, preferably of at least $1 \times 10^{-5}$ mm$^2$, more preferably of at least $1 \times 10^4$ mm and most preferably of at least $1 \times 10^{-3}$ mm$^2$. Such a structure can, for example, be obtained if for the formation of the conductive adhesive layer a dispersion according to the present invention, that in addition to components i), ii) and iii), also comprises an alkylene glycol such as ethylene glycol as component iv), is applied onto the substrate and if subsequently the dispersant iii) is removed by drying at a temperature above the glass transition temperature of the polymer of particles A). Whilst not wishing to be bound by a theory, it is believed that if such a dispersion is dried on a substrate at a temperature above the glass transition temperature of polymer IIa), the presence of polar high boiling solvents such as ethylene glycol in the dispersion somehow facilitates the annealing of neighbored particles A) while forming larger islands of polymer IIa), whereby particles IIb) of the conductive polymer, preferably the particles IIb) comprising a complex of a cationic polythiophene and a polymeric anion, are still mobile in the wet state during that stage of drying and are subsequently filling the intermediate spaces between these annealed polymer islands of polymer IIa) on ongoing drying. Such a structure leads to a particularly high ratio of electrical conductivity in lateral direction $C_{lateral}$ to the electrical conductivity in orthogonal direction $C_{orthogonal}$. In the absence of such polar high boiling solvents the particles of polymer IIa) dry comparatively fast, this drying process somehow immobilizing the particles on the surface and making an annealing of neighboured particles almost impossible.

The thickness of the conductive adhesive layer in the layered body according to the present invention is preferably in the range from 1 to 500 µm, preferably in the range from 3 to 250 µm, more preferably in the range from 4 to 150 µm and most preferably in the range from 5 to 50 µm.

According to a preferred embodiment of the layered body according to the present invention the weight ratio of polymer IIa) to the total weight of the cationic polythiophene and the polymeric anion in particles IIb) (polymer IIa):(cationic polythiophene+polymeric anion)) in the conductive adhesive layer is at least 5:1, preferably at least 10:1, more preferably at least 15:1, more preferably at least 20:1 and most preferably at least 25:1.

According to a further preferred embodiment of the layered body according to the present invention this layered body is characterized in that the conductive adhesive layer absorbs less than 10 wt. %, preferably less than 7.5 wt. %, more preferably less than 5 wt. % and most preferably less than 2.5 wt. % of water when storing the layered body for 22 hours at 25° C. and 80% rel. humidity.

A contribution towards achieving the abovementioned objects is also made by a process for producing a layered body, the process comprising α1) providing a dispersion according to the present;
α2) applying the dispersion onto at least a part of at least one surface of a substrate;
α3) at least partial removal of the dispersant iii) for the formation of a conductive adhesive layer, preferably for the formation of a conductive adhesive layer that is self-adhesive to the human skin, and that is superimposed on at least a part of at least one surface of the substrate, wherein the at least partial removal of the dispersant is accomplished by heating the dispersion that has been applied onto the substrate to a temperature above the glass transition temperature of the polymer of particles A).

In process step α1) of the process according to the present invention a dispersion according to the present invention is provided. In this context it is particularly preferred that the polymer of particles A) has a glass transition temperature of less than 35° C., preferably less than 20° C., more preferably less than 10° C. and most preferably less than 0°. In this context it is also preferred that the dispersion comprises, as component iv), an alkylene glycol such as ethylene glycol. As stated above, such a dispersion can, for example, be prepared by mixing a dispersion, preferably an aqueous dispersion, comprising the above described particles A), for example a dispersion such as RUCO-COAT® AC 1010 AQUA POLYMER AQP 275, with a dispersion, preferably an aqueous dispersion, comprising the above described particles B), for examples one of the PEDOT/PSS-dispersions that are commercially available from the Heraeus Holding GmbH, Hanau, Germany. Preferably, the above described polar high boiling compounds, particularly alkylene glycol, and optionally further additives can be added to one or both of these dispersions before they are mixed or can be added separately to the mixture of these dispersions.

In process step α2) of the process according to the present invention the dispersion is applied onto at least a part of at least one surface of a substrate. Applying the dispersion onto at least a part of at least one surface of the substrate can be accomplished by known methods, for example by spin coating, dipping, pouring, dropping on, injecting, spraying, film transfer application, knife application, spreading or printing, for example inkjet, screen, intaglio, offset or pad printing, in a wet film thickness in the range from 0.1 µm to 250 µm, preferably in the range from 0.5 µm to 50 µm.

Preferred substrates that can be used in the process according to the present invention are those substrates that have already been mentioned above as preferred substrates in connection with the layered body according to the present invention.

In process step α3) of the process according to the present invention the dispersant is at least partially removed for the formation of a conductive adhesive layer, preferably for the formation of a conductive adhesive layer that is self-adhesive to the human skin, and that is superimposed on at least a part of at least one surface of the substrate, wherein the at least partial removal of the dispersant is accomplished by heating the dispersion that has been applied onto the substrate to a temperature above the glass transition temperature of the polymer of particles A). Partial removal of the dispersant iii) can be achieved by simply drying the superimposed layer, preferably by heating the substrate to a temperature in the range from, for example, 35 to 200° C., preferably 75 to 150° C.

A contribution towards achieving the abovementioned objects is also made by a layered body obtainable by the process according to the present invention. Preferably, the properties of this layered body are identical to the properties of the layered body according to the present invention that have been described above.

Accordingly, the layered body that is obtainable by the process according to the present invention is preferably characterized in that the conductive adhesive layer comprises a matrix of the polymer of particles A), in which the particles B) of the conductive polymer, preferably the particles of a complex of a cationic polythiophene and a polymeric anion, that are distributed. In this context it is also preferred that the conductive adhesive layer comprises a plurality of islands of the polymer IIa), the islands having a size of at least $1 \times 10^{-6}$ mm$^2$, preferably of at least $1 \times 10^{-5}$ mm$^2$, more preferably of at least $1 \times 10^{-4}$ mm$^2$ and most preferably of at least $1 \times 10^{-5}$ mm$^2$.

Furthermore, the layered body that is obtainable by the process according to the present invention is preferably characterized in that the conductive adhesive layer is characterized by a specific resistance in transversal direction ($R_{transversal}$) of less than 500 Ωm, preferably less than 100 Ωm and most preferably less than 50 Ωm,
and
a specific resistance in lateral direction ($R_{lateral}$) of less than 5000 Ωm, preferably less than 50 Ωm and most preferably less than 5 Ωm.

In addition to this the layered body that is obtainable by the process according to the present invention is preferably characterized in that the conductive adhesive layer absorbs less than 10 wt. %, preferably less than 7.5 wt. %, more preferably less than 5 wt. % and most preferably less than 2.5 wt. % of water when storing the layered body for 22 hours at 25° C. and 80% rel. humidity.

A contribution towards achieving the abovementioned objects is also made by the use of the layered body according to the present invention or of the layered body that is obtainable by the process according to the present invention for electrophysical measurements, wherein the conductive adhesive layer comes into direct contact with the skin. Preferred electrophysical measurements comprise electrocardiography (ECG), electroencephalography (EEG), electrical impedance tomography (ET), electromyography (EMG) and electro-oculography (EOG).

A contribution towards achieving the abovementioned objects is also made by a therapeutic current delivery or current receiving system comprising:
- a therapeutic current delivery or current receiving device;
- at least one cable connector connected to the therapeutic current delivery or current receiving device;
- at least one electrode comprising a layered body to the present invention or made from a layered body that is obtainable by the process according to the present invention.

The therapeutic current delivery or current receiving device can be any type of monitoring or stimulation device that is known to the person skilled in the art, such as, for example, an electrograph (ECG) device, an electroencephalograph device, an electromyography device, a transcutaneous electrical nerve stimulation device, an electrical muscle stimulation device, a neuromuscular stimulation devices, or a functional electrical stimulation device.

The invention is now explained in more detail with the aid of test methods and non-limiting figures and examples.

Figure 1:
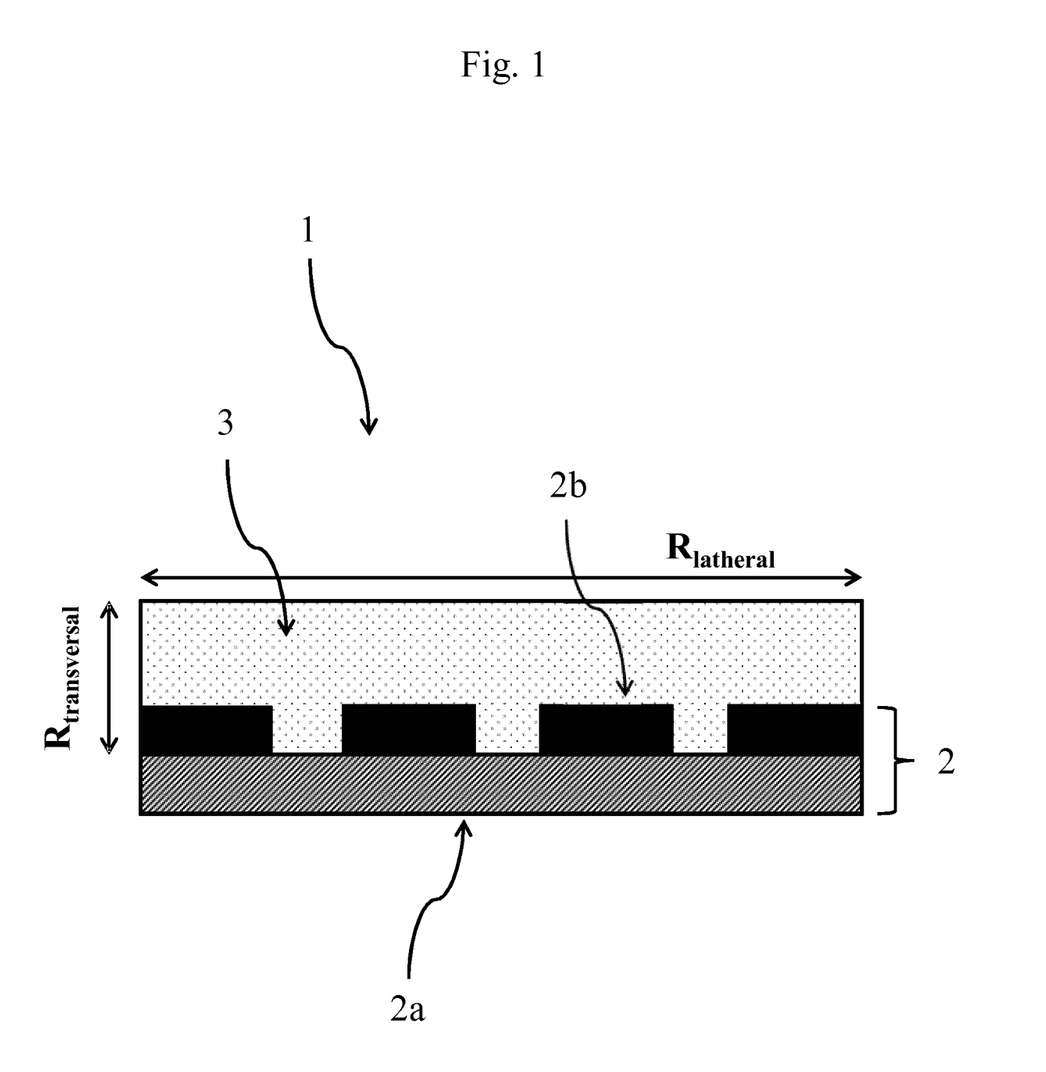
FIG. 1 shows a cross section of a preferred layered body according to the present invention.
Figure 2:
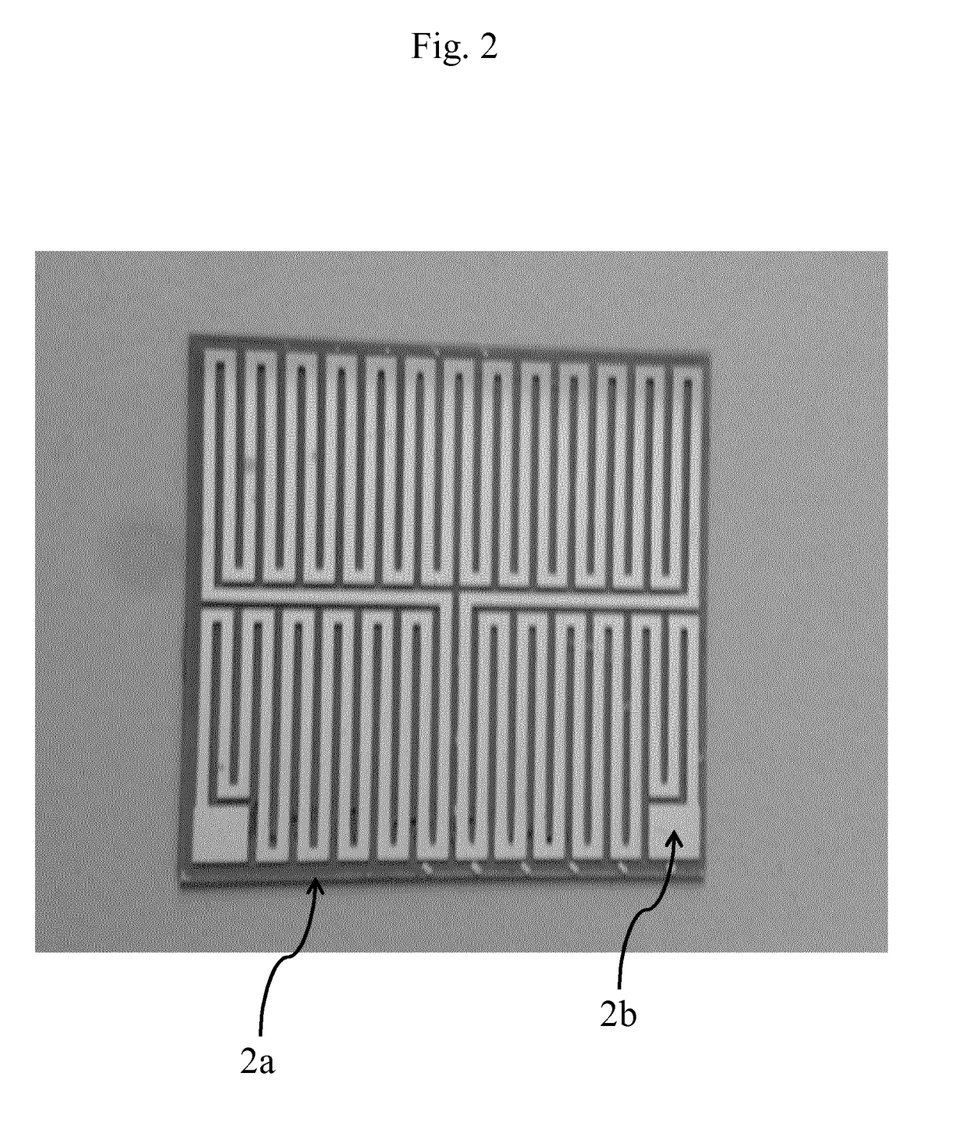
FIG. 2 shows a substrate that can be used for the formation of a layered body according to the present invention from the top.

As can be seen in FIGS. 1 and 2, the layered body 1 according to the present invention comprises a substrate 2 onto which the conductive adhesive layer 3 according to the present invention is superimposed. Substrate 2 preferably comprises a non-conductive polymer layer 2a, which in the examples of the present application is a thin polyimide-film, onto which a further conductive layer 2b is superimposed. In the examples of the present application the further conductive layer 2b is a silver grid that has been applied onto the polyimide-film by means of a silver paste.

EXAMPLES

Test Methods:
Determination of the $d_{50}$-Value of Particles A) and Particles B)

The $d_{50}$-value for particles A) and particles B) is determined via ultracentrifugation. The details of the method are described under Schlotan et al. (Kolloid-Z und Z Polymer; 250 (1972) page 782, "Bestimmung der Teilchengrößenverteilung von Latices mit der Ultrazentrifuge") and Müller (Colloid & Polymer Science: 267 (1989) page 1113). If required, particles A) and/or particles B) can be separated from other particles that may interfere with the determination of the $d_{50}$-value by techniques known to the person skilled in the art, such a density gradient centrifugation, gel permeation chromatographie or gel electrophoresis.
Determination of the Glass Transition Temperature The glass transition temperature is measured by means of differential calorimetry (DSC) (ISO 11357-2). This is, strictly speaking, a glass transition region, which extends over a temperature range. The glass transition temperatures referred to in the present invention represents average values.
Determination of Moisture Absorption Between 8 and 9 g of the dispersion according to the present invention were given in an aluminium tray and the tray is dried at a temperature of 120° C. for 135 minutes in an oven with recirculating air. A dried films remains in the tray the weight of which is determined by weighing ($tray_{before\ storage}$).

Subsequently, the aluminium tray is stored in a closed desiccator at a temperature of 25° C. at 80% rel. humidity that is created with the aid of a saturated salt solution. After 22 hours the aluminium tray is weight again ($tray_{after\ storage}$) and the moisture absorption (in wt. %) is calculated as follows:

Moisture absorption=100%×($tray_{after\ storage}$−$tray_{before\ storage}$)/$tray_{before\ storage}$ Determination of the Lateral and Transversal Resistance The specific resistance of the conductive adhesive layer in the lateral direction ($R_{lateral}$) is determined by measuring the surface resistance (in Ω/sq.) by means of an ACL 800 Digital Megohmmeter (ACL Staticide, Chicago, IL, USA). The specific resistance is calculated by multiplying the surface resistance with the thickness of the conductive adhesive layer (in m). The thickness of the conductive adhesive layer is calculated on the basis of the solid content of the dispersion used to prepare the conductive adhesive layer and the wet film thickness in which the dispersion is applied onto the substrate.

The specific resistance of the conductive adhesive layer in the transversal direction ($R_{transversal}$) is determined by impedance spectrometry using a SP-300 potentiostat/galvanostat (Bio-Logic SAS, Claix, France). A platinum electrode that was attached onto the surface of the conductive adhesive layer served as the counter electrode for a silver grid electrode that was located beneath the conductive adhesive layer. The specific resistance of the conductive adhesive layer in the transversal direction was determined at a frequency of 1 kHz.

Example 1: Preparation of Conductive Adhesive Compositions

Mixtures of conductive polymer, anionic acrylic ester copolymer dispersion and optionally ethylene glycol were prepared. For that purpose a highly conductive aqueous PEDOT/PSS-dispersion (Clevios™ P HC V6 Screen:solids content 1 wt. %) was introduced into a in a beaker.

Subsequently, aqueous acrylate dispersions Rucocoat AC 1010 (solids content 65 wt. %), AQP 275 (solids content 60 wt. %) and Acronal S728 (solids content 50 wt. %) were added dropwise, followed by the addition of ethylene glykol. The mixtures were subsequently stirred for 30 minutes.

| Sample | PEDOT:PSS-dispersion [g/g] | Rucocoat AC 1010 [g/g] | AQP 275 [g/g] | Acronal S728 [g/g] | ethylene glykol [g/g] | solids content (calculated) [wt. %] |
|---|---|---|---|---|---|---|
| A | 10 | 20 | — | — | 1 | 42 |
| B | 4 | 20 | — | — | 0.4 | 53 |
| C | 10 | 10 | — | — | 1 | 31 |
| D | 10 | 10 | — | — | 0 | 33 |
| E | 20 | 10 | — | — | 2 | 21 |
| F | 10 | — | 10 | — | 1 | 29 |
| G | 10 | — | — | 10 | 1 | 24 |

For the characterization, the samples were coated onto a Melinex PET film substrate by means of a manual squeegee with a wet film thickness of 40 μm and dried for 5 minutes at 120° C. in a forced-air drying cabinet. The electrical surface resistance (Ohm/sq; ACL 800, Staticide) was measured and the adhesive force was determined qualitatively with the fingers (finger pressure/number of fingers need to lift the film having a size of about 20 cm×30 cm). Furthermore, adhesive layers prepared by means of these samples were analyzed with respect to the moisture absorption of dried films that have been prepared with these samples.

| Sample | surface resistance [Ohm/sq] | adhesive force | relative thickness of the film (calculated) | amount of conductive polymer in the film (calculated) [wt. %] | moisture absorption [wt. %] |
|---|---|---|---|---|---|
| A | $6 \times 10^5$ | strong | 1.4 | 0.8 | |
| B | $2 \times 10^8$ | very strong | 1.75 | 0.3 | 1.6 |
| C | $2 \times 10^5$ | medium | 1 | 1.5 | |
| D | $3 \times 10^7$ | medium | 1 | 1.5 | 2.1 |
| E | $2 \times 10^3$ | weak | 0.7 | 3.0 | 3.2 |
| F | $5 \times 10^3$ | medium | 1 | 1.6 | |
| G | n. d. | not adhesive | 0.8 | 2.0 | |

Example 2: Preparation of Electrode

A glass support substrate was coated with PAA (polyamidocarboxylic acid) which was subsequently thermally polycondensed to give PI (polyimide). The resulting polymer film has a thickness of 10 µm. A silver paste on a PI-basis for potential homogenization was then screen printed by means of screen printing as shown in FIG. 2.

This system was subsequently coated with the samples A to G obtained in Example 1. For this purpose, the samples were coated on the polyimide electrode substrate with a 90 µm wet film thickness by lacquer coating and were subsequently dried for 5 minutes at 120° C. in a circulating air drying cabinet. This operation was performed a second time to obtain a thick conductive adhesive layer. The samples thus obtained were provided with a non-polarized electrode made of Pt-foil in order to test the impedance behavior in the range of 5 MHz to 100 mHz. All samples showed a purely ohmic behavior with a slightly inductive component which, however, is caused by the leads.

As a comparison reference, the real part of the resistance was used at 1 kHz, which represents a suitable guide number for physiological systems. The determined values were additionally surface-normalized by the electrode surfaces of 44×51 mm. The following values have been measured:

| Sample used for layer preparation | Re at 1 kHz [Ohm] | rho at 1 kHz [Ohm/cm$^2$] |
|---|---|---|
| A | 1.27 | 28.38704 |
| B | 1.44 | 32.18688 |
| C | 1.43 | 31.96336 |
| D | 3.27 | 73.09104 |
| E | 0.73 | 16.31696 |
| F | 0.36 | 8.04672 |
| G | 0.62 | 13.85824 |

In the following table the specific resistance in both, the lateral and the transversal direction, for the conductive adhesive layers that have been made with Samples A, B, C, D and E are listed:

| Sample used for layer preparation | $R_{transversal}$ [Ohm × m] | $R_{lateral}$ [Ohm × m] |
|---|---|---|
| A | 45.8 | 10.08 |
| B | 82.0 | 4240 |
| C | 31.7 | 2.48 |
| D | 14.7 | 396 |
| E | 27.8 | 0.024 |

As can be seen, the addition of ethylene glycol has an influence on the orientation of the PEDOTIPSS from anisotropic orthogonal to lateral conductivity. By adding ethylene glycol the proportion of the required metal grid on the flexible substrate can thus be reduced.

Compared to the electrodes of the prior art the electrodes according to the present invention show purely ohmic behavior and the relevant resistances are also lower than for the known electrolyte-based electrode systems.

The invention claimed is:
1. A dispersion comprising
    i) particles A) of polymer comprising repeating units having the general structure —CH$_2$—CR$^1$—COOR$^2$— wherein
        R$^1$ represent H or an alkyl group, and
        R$^2$ represents an optionally substituted C$_1$-C$_{10}$-alkyl group,
        wherein particles A) have a mass average particle diameter (d$_{50}$) of at least 800 nm;
    ii) particles B) of a conductive polymer,
        wherein the particles B) have a mass average particle diameter of less than 150 nm;
    iii) at least one dispersant;
    wherein the weight ratio of the polymer in particles A) to the conductive polymer in particles B) is at least 15:1.
2. The dispersion according to claim 1, wherein the polymer of particles A) has a glass transition temperature of less than 35° C.
3. The dispersion according to claim 1, wherein R$^1$ is H and R$^2$ is selected from the group consisting of —CH$_3$, —CH$_2$CH$_3$, —C$_4$H$_9$, —CH$_2$CH(C$_2$H$_5$)(C$_4$H$_9$) and —C$_8$H$_{17}$.
4. The dispersion according to claim 1, wherein at least 25% of the repeating units in the polymer of particles A) are monomers in which R$^1$ is H and R$^2$ is selected from the group consisting of —CH$_3$, —CH$_2$CH$_3$, —C$_4$H$_9$, —CH$_2$CH(C$_2$H$_5$)(C$_4$H$_9$) and —C$_8$H$_{17}$, based on the total number of repeating units in the polymer of particles A).
5. The dispersion according to claim 1, wherein the polymer of particles A) is a copolymer of acrylic acid or a salt of acrylic acid or both and an acrylic acid ester selected from the group consisting of methyl acrylate, ethyl acrylate, n-butyl acrylate, 2-ethylhexylacrylate and n-octyl acrylate.
6. The dispersion according to claim 1, wherein the conductive polymer of particles B) comprises a PEDOT/PSS-complex.
7. The dispersion according to claim 1, wherein the dispersion further comprises, as component iv), a polar high boiling compound having a boiling point (at 1013 mbar) of at least 120° C.
8. A process for producing a layered body, the process comprising
    α1) providing a dispersion as defined in claim 2;
    α2) applying the dispersion onto at least a part of at least one surface of a substrate;
    α3) at least partial removal of the dispersant iii) for the formation of a conductive adhesive layer that is super- imposed on at least a part of at least one surface of the substrate, wherein the at least partial removal of the dispersant is accomplished by heating the dispersion that has been applied onto the substrate to a temperature above the glass transition temperature of the polymer of particles A).

9. The dispersion according to claim 1, wherein the dispersant is water.

10. The dispersion according to claim 1, wherein particles B) of a conductive polymer are particles B) of a complex of a cationic polythiophene and a polymeric anion.

11. The dispersion according to claim 10, wherein the weight ratio of the polymer in particles A) to the total weight of the cationic polythiophene and the polymeric anion in the complex of particles B) is at least 15:1.

12. The dispersion according to claim 7, wherein the dispersion further comprises, as component iv), ethylene glycol.

* * * * *